United States Patent
Obermiller et al.

(10) Patent No.: US 10,420,636 B2
(45) Date of Patent: Sep. 24, 2019

(54) STENT GRAFT DEVICES HAVING COLLAGEN COATING

(75) Inventors: F. Joseph Obermiller, West Lafayette, IN (US); Clay D. Fette, Palm Beach Gardens, FL (US)

(73) Assignee: Cook Medical Technologies LLC, Bloomington, IN (US)

( * ) Notice: Subject to any disclaimer, the term of this patent is extended or adjusted under 35 U.S.C. 154(b) by 729 days.

(21) Appl. No.: 11/500,697

(22) Filed: Aug. 8, 2006
(Under 37 CFR 1.47)

(65) Prior Publication Data

US 2007/0112411 A1      May 17, 2007

Related U.S. Application Data

(63) Continuation of application No. PCT/US2005/003967, filed on Feb. 9, 2005.

(60) Provisional application No. 60/543,482, filed on Feb. 9, 2004.

(51) Int. Cl.
| | | |
|---|---|---|
| *A61F 2/07* | (2013.01) | |
| *A61L 27/34* | (2006.01) | |
| *A61L 27/36* | (2006.01) | |
| *A61F 2/06* | (2013.01) | |
| *A61F 2/88* | (2006.01) | |
| *A61F 2/90* | (2013.01) | |
| *A61F 2/915* | (2013.01) | |

(52) U.S. Cl.
CPC .............. *A61F 2/07* (2013.01); *A61L 27/34* (2013.01); *A61L 27/3629* (2013.01); *A61L 27/3633* (2013.01); *A61L 27/3691* (2013.01); *A61F 2/88* (2013.01); *A61F 2/90* (2013.01); *A61F 2/915* (2013.01); *A61F 2002/065* (2013.01); *A61F 2002/072* (2013.01); *A61F 2002/075* (2013.01)

(58) Field of Classification Search
CPC ................. A61F 2/07; A61F 2002/072; A61F 2002/077; A61F 2002/65; A61F 2002/065
USPC ................................. 623/1.13, 1.16
See application file for complete search history.

(56) References Cited

U.S. PATENT DOCUMENTS

| | | |
|---|---|---|
| 2,127,903 A | 8/1938 | Bowen |
| 3,562,820 A | 2/1971 | Bernhard |
| 3,587,586 A * | 6/1971 | Kronenthal .................. 606/154 |
| 4,902,508 A | 2/1990 | Badylak |
| 4,956,178 A | 9/1990 | Badylak et al. |
| 5,141,747 A | 8/1992 | Scholz |
| 5,275,826 A | 1/1994 | Badylak et al. |
| 5,281,422 A | 1/1994 | Badylak et al. |
| 5,372,821 A | 1/1994 | Badylak et al. |

(Continued)

FOREIGN PATENT DOCUMENTS

| | | |
|---|---|---|
| AU | 2003295797 B2 | 6/2004 |
| EP | 1217101 A | 6/2002 |

(Continued)

*Primary Examiner* — Sarah A Simpson
(74) *Attorney, Agent, or Firm* — Woodard, Emhardt, Henry, Reeves and Wagner LLP

(57) ABSTRACT

Described are stent graft devices and methods for their preparation and use. Expandable stent graft devices of the invention include inner and/or outer coverings uniquely applied and associated with surfaces of the stent. In certain described embodiments, bioremodelable materials such as ECM materials are vacuum pressed onto and/or around elements of a stent in the manufacture of a stent graft device.

28 Claims, 14 Drawing Sheets

(56) References Cited

U.S. PATENT DOCUMENTS

| | | |
|---|---|---|
| 5,352,463 A | 10/1994 | Badylak et al. |
| 5,445,833 A | 8/1995 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,641,518 A | 6/1997 | Badylak et al. |
| 5,645,860 A | 7/1997 | Knapp et al. |
| 5,695,998 A | 12/1997 | Badylak et al. |
| 5,711,969 A | 1/1998 | Patel et al. |
| 5,753,267 A | 5/1998 | Badylak et al. |
| 5,755,791 A | 5/1998 | Whitson et al. |
| 5,762,966 A | 6/1998 | Knapp et al. |
| 5,763,416 A | 6/1998 | Bonadio et al. |
| 5,885,619 A | 3/1999 | Patel et al. |
| 5,955,110 A | 9/1999 | Patel et al. |
| 5,997,575 A | 12/1999 | Whitson et al. |
| 6,087,157 A | 7/2000 | Badylak et al. |
| 6,096,347 A | 8/2000 | Geddes et al. |
| 6,099,567 A | 8/2000 | Badylak et al. |
| 6,126,686 A | 10/2000 | Badylak et al. |
| 6,187,039 B1 | 2/2001 | Hiles et al. |
| 6,206,931 B1 | 3/2001 | Cook et al. |
| 6,241,981 B1 | 6/2001 | Cobb et al. |
| 6,264,992 B1 | 7/2001 | Voytik-Harbin et al. |
| 6,331,319 B1 | 12/2001 | Badylak et al. |
| 6,358,284 B1 | 3/2002 | Fearnot et al. |
| 6,375,989 B1 | 4/2002 | Badylak et al. |
| 6,475,232 B1 | 11/2002 | Babbs et al. |
| 6,537,310 B1* | 3/2003 | Palmaz et al. ............. 623/1.13 |
| 6,660,033 B1* | 12/2003 | Marcade et al. ............ 623/1.16 |
| 6,666,892 B2 | 12/2003 | Hiles et al. |
| 6,808,533 B1* | 10/2004 | Goodwin ............... A61F 2/86 |
| | | 623/1.13 |
| 7,175,652 B2* | 2/2007 | Cook et al. ............... 623/1.13 |
| 2002/0193864 A1* | 12/2002 | Khosravi et al. ........... 623/1.13 |
| 2003/0051735 A1 | 3/2003 | Pavcnik et al. |
| 2003/0065379 A1* | 4/2003 | Babbs et al. ............... 623/1.13 |
| 2003/0199969 A1* | 10/2003 | Steinke et al. ............. 623/1.16 |
| 2004/0176832 A1* | 9/2004 | Hartley et al. ............. 623/1.11 |

FOREIGN PATENT DOCUMENTS

| | | |
|---|---|---|
| GB | 887844 | 1/1962 |
| WO | WO 1995/22611 | 8/1995 |
| WO | WO 1996/24661 | 8/1996 |
| WO | WO 1996/25179 | 8/1996 |
| WO | WO 1996/32146 | 10/1996 |
| WO | WO 1998/25636 | 6/1998 |
| WO | WO 1998/26291 | 6/1998 |
| WO | WO 2000/32112 | 6/2000 |
| WO | WO 2000/32250 | 6/2000 |
| WO | WO 2000/32253 | 8/2000 |
| WO | WO 2001/10355 | 2/2001 |
| WO | WO 2001/54625 | 8/2001 |
| WO | WO 2001/56500 | 8/2001 |
| WO | WO 2003/002165 | 1/2003 |
| WO | WO 2003/002168 | 1/2003 |
| WO | WO 2003/009764 | 2/2003 |
| WO | PCT/US2003/065379 A1 | 4/2003 |
| WO | WO 2003/035125 | 5/2003 |
| WO | WO 2003/088844 | 10/2003 |
| WO | WO 2003/092471 | 11/2003 |
| WO | WO 2003/092546 | 11/2003 |
| WO | WO 2004/047687 A1 | 6/2004 |
| WO | PCT/US2004/176833 A1 | 9/2004 |

* cited by examiner

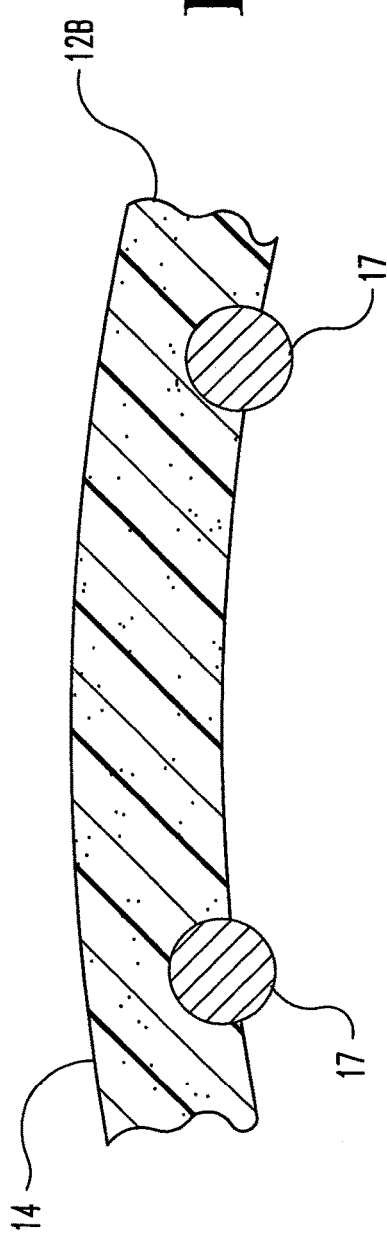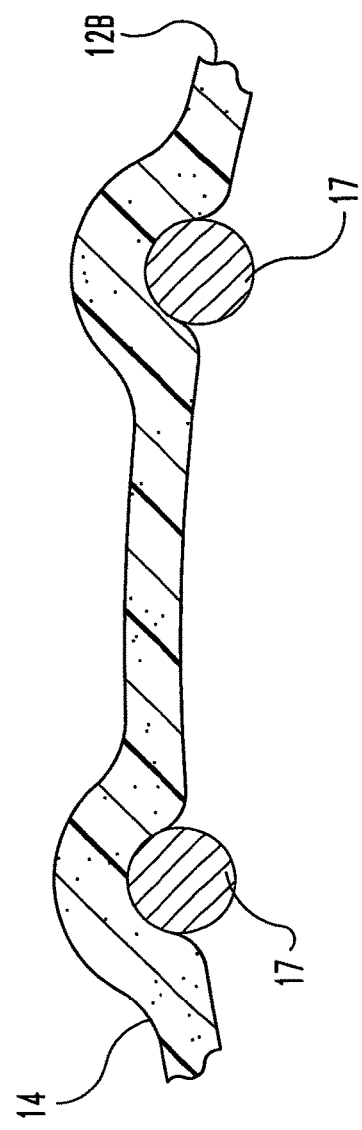

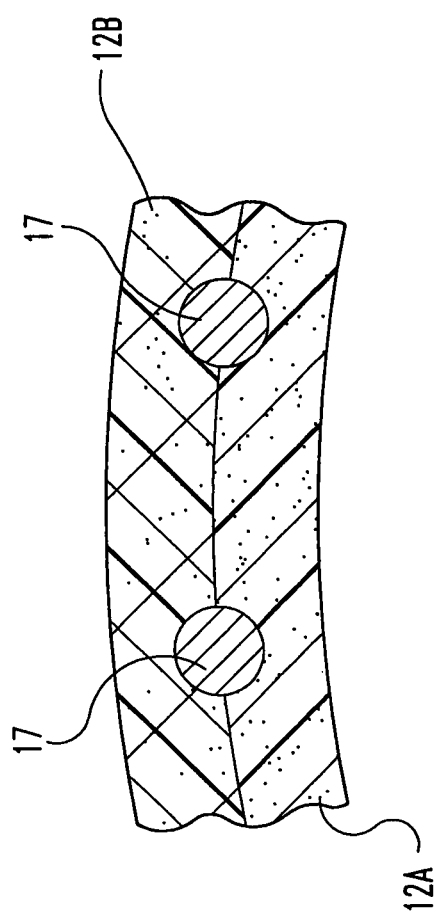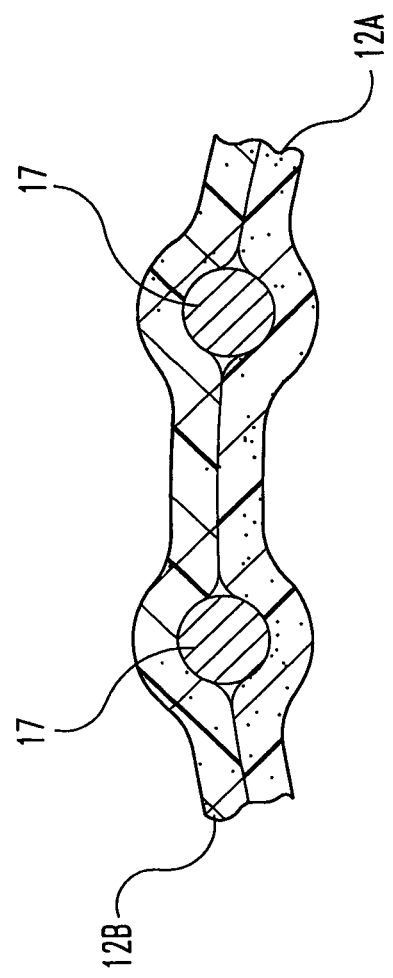

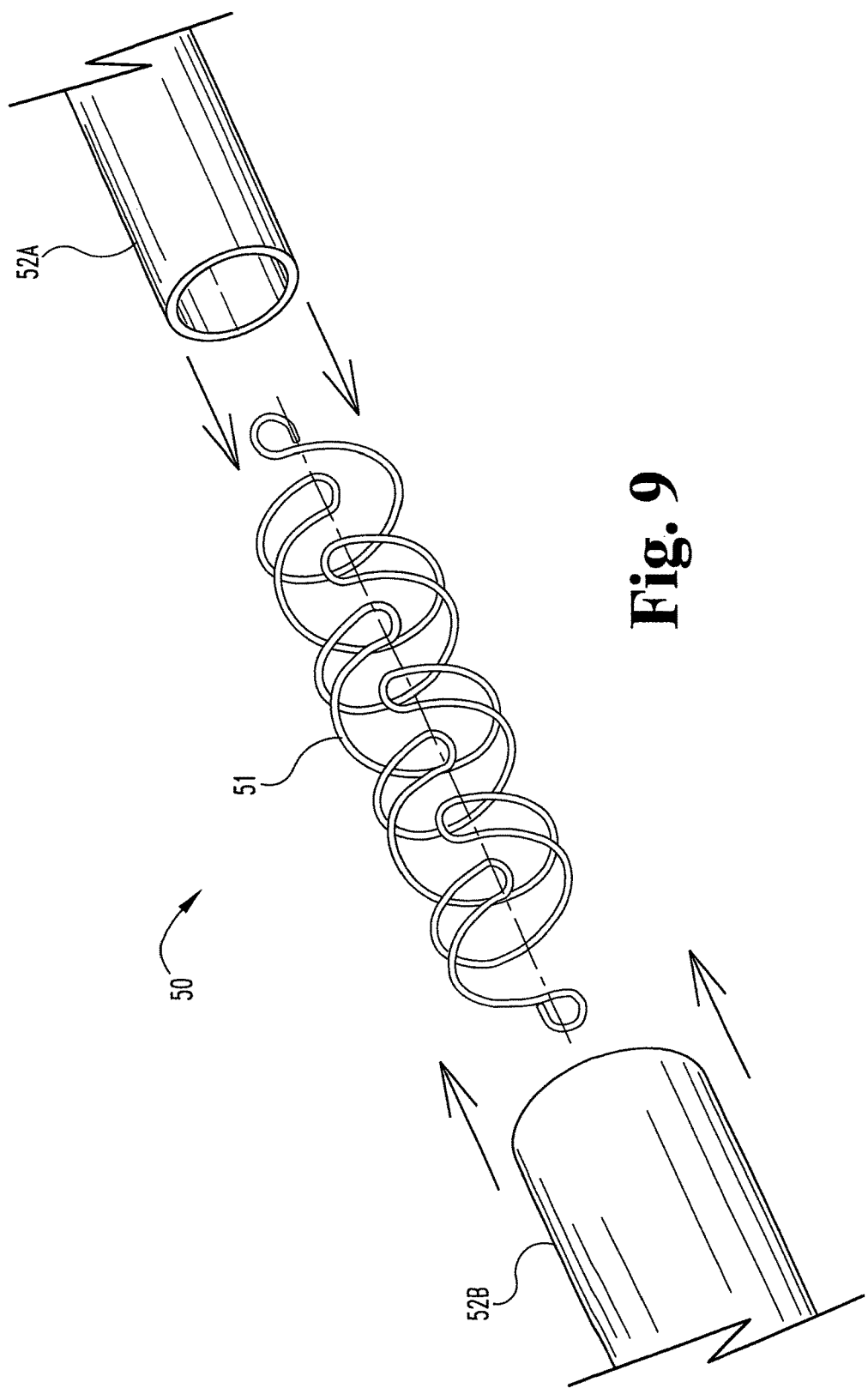

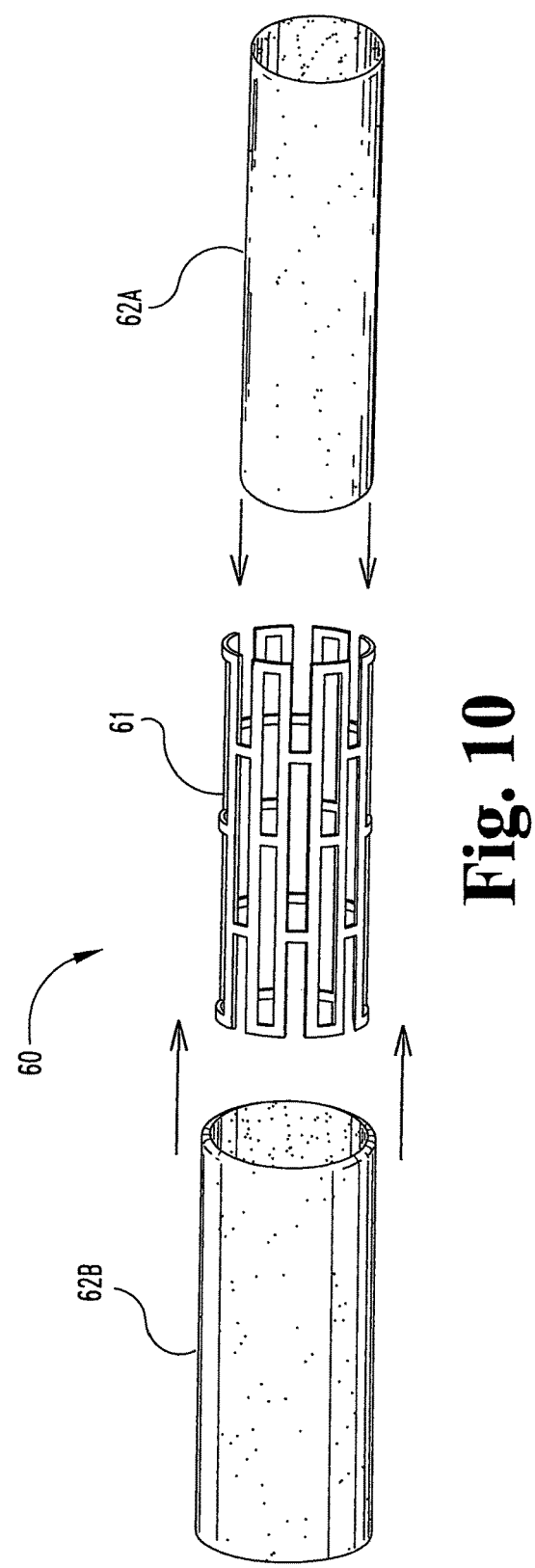

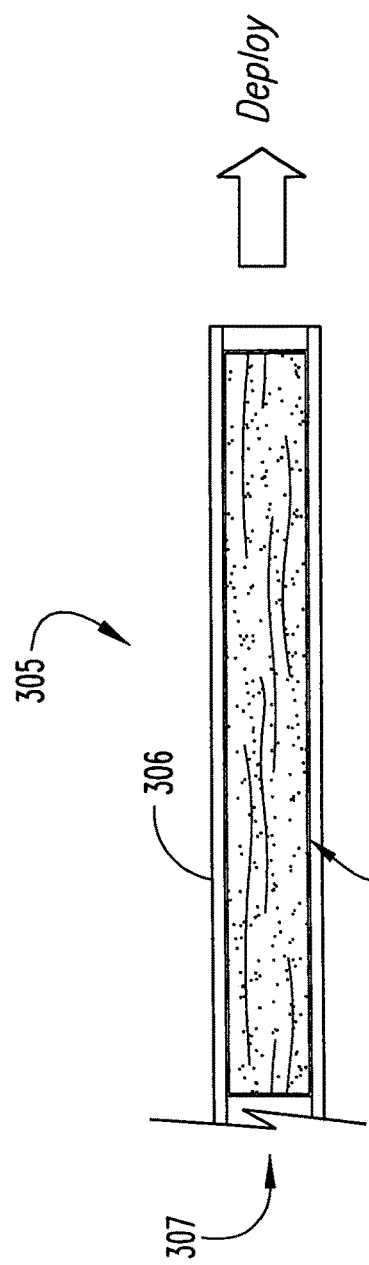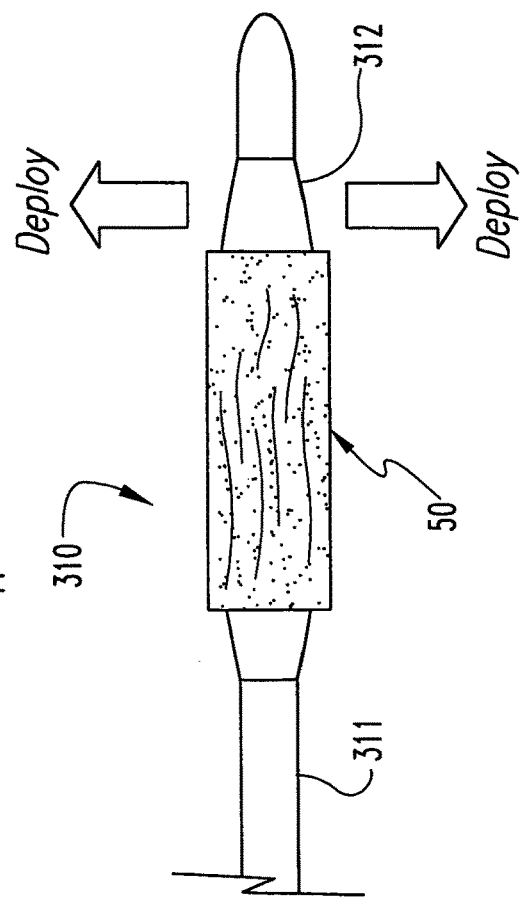

STENT GRAFT DEVICES HAVING COLLAGEN COATING

REFERENCE TO RELATED APPLICATIONS

This application is a continuation application of International Application No. PCT/US2005/003967 filed Feb. 9, 2005 (which was published in English), which claims the benefit of U.S. Patent Application Ser. No. 60/543,482 filed Feb. 9, 2004, each of which is hereby incorporated by reference in its entirety.

BACKGROUND

The present invention relates generally to implantable medical devices, and in one particular aspect to implantable stent graft devices that include a stent, and a covering on at least part of the stent.

As further background, stent graft devices having covering material on a stent are known. Although a number of techniques for attaching covering material to a stent have been suggested, in practice, most commonly the covering material has been attached to the stent entirely by suturing. The present invention provides devices and methods addressing the attachment of covering material to a stent in that provide a unique association of the covering material with the stent, and in some cases can avoid or reduce the need for suture attachments.

SUMMARY

In certain aspects, the present invention provides implantable stent graft devices that include a biocompatible covering material uniquely associated with at least a portion of the stent, for example wherein the covering material contours to and/or embeds elements of the stent.

In one form, the invention provides a stent graft device that includes a tube of bioremodelable graft material, and a stent. At least a portion of said stent is embedded within the tube of bioremodelable graft material.

In another aspect, the invention provides a stent graft device including a radially expandable stent, an exterior collagenous covering on an exterior surface of the stent, and an interior collagenous covering on an interior surface of the stent. The exterior collagenous covering is bonded to the interior collagenous covering, and the exterior and interior collagenous coverings having surfaces locally contoured to elements of the stent.

In still another aspect, the invention concerns a method for providing a covering on at least a portion of a radially expandable stent. The method includes providing a radially expandable stent and, forcing a hydrated, bioremodelable covering material against a surface of the stent sufficiently to locally contour surfaces of the bioremodelable covering material against elements of the stent. The bioremodelable covering material is dried while forced against the surface of the stent.

In another form, the invention provides a method for providing a covering on at least a portion of a stent. A stent is provided and a hydrated, bioremodelable covering material including a multilaminate construct is forced against a surface of the stent. The bioremodelable covering material is dried while forced against the surface of the stent.

Another embodiment of the invention relates to a method for providing a covering on at least a portion of a stent. The method includes providing an assembly having a stent and a hydrated covering material positioned on a surface of the stent. The assembly is subject to vacuum drying to provide the covering on the stent.

In another form, the invention provides a method for applying a covering on a surface of at least a portion of a stent. An assembly is provided having a stent and a covering material in a relatively conformable condition positioned on a surface of the stent. The assembly is positioned in a chamber. Wall surfaces of the chamber are collapsed to force the covering material against the surface of the stent while the covering material is in its relatively conformable condition. The covering material is caused to change to a relatively non-conformable condition while forced against the surface of the stent.

Another aspect of the invention provides a method for providing a covering on at least a portion of a radially expandable stent. The method comprises providing a radially expandable stent and forcing a hydrated, bioremodelable covering material against a surface of the stent. The method also includes lyophilizing the bioremodelable covering material while forced against the stent surface.

In another aspect, the present invention provides a method for making a stented graft construct. The method comprises providing an assembly having at least a first stent and at least a second stent, wherein the stents are discrete and spaced from one another. The assembly further includes one or more pieces of hydrated collagenous covering material and/or another similar covering material susceptible to dehydration-induced bonding, arranged so as to interconnect the stents, wherein the hydrated covering material includes portions at least partially surrounding the first stent and the second stent between inner and outer layers of the covering material. The method further includes drying the hydrated covering material so as to bond the inner and outer layers to one another and entrap and interconnect the first stent and the second stent. In a preferred forms, the drying comprises vacuum pressing and/or lyophilizing the assembly.

In another embodiment, the invention provides a stented graft construct that includes a plurality of discrete, spaced stents. The discrete, spaced stents are interconnected to one another by inner and outer layers of a bioremodelable covering material. At least one of (and potentially both of) the inner and outer layers includes a multilaminate construct.

In a further aspect, the invention provides a stented graft construct that includes a plurality of discrete, spaced stents interconnected to one another by inner and outer layers of a bioremodelable covering material. The inner and outer layers are bonded to one another and entrap and interconnect the discrete, spaced stents. In certain embodiments, at least one of (and potentially both of) the inner and outer layers includes a multilaminate construct, and/or the inner and outer layers are dehydrothermally bonded to one another, e.g. by vacuum pressing and/or lyophilization conditions.

Additional embodiments as well as features and advantages of the present invention will be apparent from the descriptions herein.

DESCRIPTION OF THE FIGURES

FIGS. 6A, 6B, 7A, 7B, 8A and 8B illustrate various embodiments of covering/stent element configurations of the invention.

FIGS. 9-11 illustrate the components of various stent grafts of the invention.

FIGS. 13-14 provide illustrations of modes of deployment of stent grafts of the invention.

DETAILED DESCRIPTION

Figure 1:
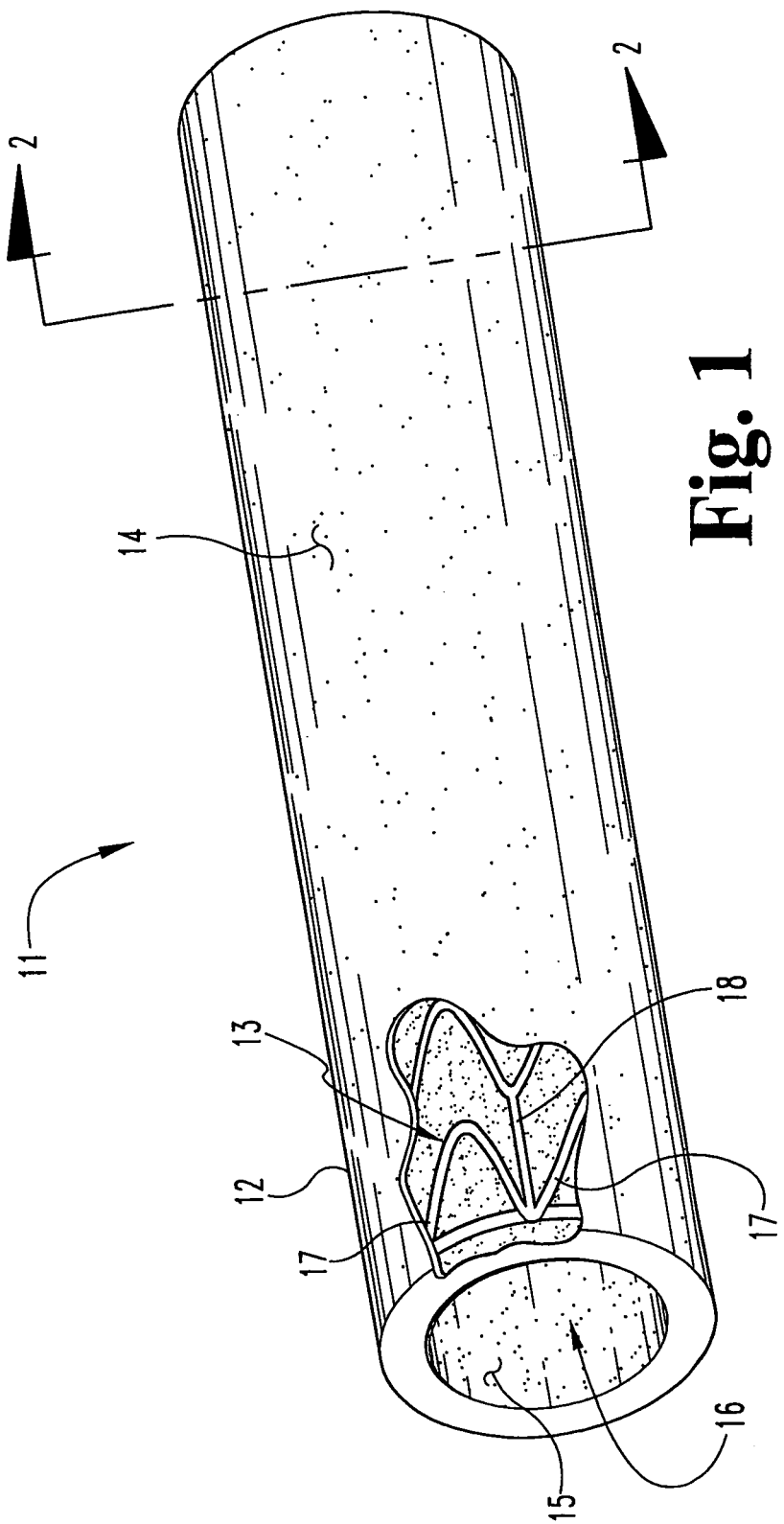
FIG. 1 provides a perspective partial cut-away view of one stent graft embodiment of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, in one aspect, the present invention provides graft devices for implantation in a patient, for example within a bodily lumen. Certain embodiments of the invention provide stent graft devices that include at least one expandable member, e.g. a stent, and a graft material forming a covering on all or a part of inner and/or outer surfaces of the expandable member.

Illustratively, the expandable member(s) incorporated into graft devices of the invention may be any one of wide variety of stent devices that have been or are currently commercially available. Stent devices provide a supporting framework structure that may take many forms. Open or perforate stents are known, which may include a network of struts or wire-like elements. The stent device used in the present invention may be of any suitable design, including for example both forcibly expandable and self-expanding stents. As is known, forcibly expandable stents can be provided and delivered in a contracted state, and then expanded upon the application of a force, e.g. an outward radial force, to the stent. Commonly, the outward radial force is provided by an expandable member, such as a balloon, received within the contracted stent structure. Several such "balloon-expandable" stents are currently available on the commercial market. Self-expanding stents can be designed so as to be configurable to and held in a contracted state for delivery, and then released at a target site, whereupon they expand on their own. Stents are also known that take on a contracted state, but expand in response to a conditional change, e.g. a change in temperature such as may be incurred in a temperature transition from a first temperature below the body temperature of a patient, to the body temperature of the patient. Stents having these or other characteristics may be used in embodiments of the present invention.

Stents or other expandable support members may be made from metallic or non-metallic material, or both. The non-metallic material can suitably be a synthetic polymeric material, including for example bioresorbable and/or non-bioresorbable plastics. Materials commonly used in stent construction include biologically compatible metals, e.g. stainless steel, titanium, tantalum, gold, platinum, copper and the like, as well as alloys of these metals; synthetic polymeric materials; low shape memory plastic; a shape-memory plastic or alloy, such as nitinol; and the like.

Just to identify a few non-limiting examples, suitable stents for use in the invention include the Zilver stent, Gianturco-Roubin stent, the Palmaz-Schatz stent, Wallstent, Mammotherm stent, Symphony stent, Smart stent, Perflex, AVE, Intrastent, and Herculink stents, self-expanding Instent, Gianturco Z-stent, Ultraflex nitinol mesh stent, Esophacoil stent, Gianturco Z tracheobronchial tree stent, and the Wallstent tracheobronchial endoprosthesis.

Certain embodiments of the invention provide medical devices including an expandable member, e.g. as described above, associated with a full or partial covering of material on an inner and/or outer surface of the expandable member. In some embodiments, the covering material is associated in a unique manner with the expandable member. For example, the covering material may be contoured snugly around or completely embed elements of the expandable member to assist in maintaining the attachment of the covering material to the expandable member. This may avoid, reduce, or simplify the need for other mechanical attachments, such as sutures, to hold the covering material to the expandable member. It may also in some forms provide a unique, relatively fixed association of the covering material with the expandable member or elements thereof, even during contraction and/or expansion of the expandable member.

In one embodiment of the invention, the covering material is attached to the stent or other expandable member by pressing or otherwise forcing the covering material against surfaces of the expandable member while the covering material is in a relatively conformable state, and then converting the covering material to a less conformable state. In this manner, the covering material while conformable can locally contour to elements of the expandable member, e.g. struts or other wire-like elements of a stent, and when converted to its relatively less conformable state will maintain that contour to the elements of the expandable member. As a result, the attachment of the covering material to the expandable member will be facilitated. Further, the covering material may have at least some shape memory properties such that if converted back to a conformable state, a contoured relation between the elements of the expandable member and the covering material will still exist.

In preferred aspects of the invention, the covering material will be hydratable, and will be relatively more conformable when hydrated than when dried. In this fashion, the covering material while in a hydrated state can be forced against an inner and/or outer surface of the expandable member sufficiently to locally contour the covering material to elements of the expandable member, and then dried while maintaining that force to achieve an attachment of the covering material to the expandable member. Advantageously, a vacuum pressing operation can be utilized to both force the covering material against the expandable member and to dry the covering material.

In other embodiments of the invention, covering material positioned upon one side of the expandable member (e.g. inside or outside the lumen of a stent) can be attached through open areas of the expandable member to a material on the other side of the expandable stent, so as to facilitate attachment of the covering material to the expandable element. In some inventive forms, the attachment of the two opposing materials can be over essentially all contacting areas of the two materials, so as to effectively fix the relation between entrapped elements of the expandable member and the covering, so that no substantial sliding of the elements within the surrounding covering is observed. In still other forms, the two opposed materials can be attached to one another in a manner including fusion of the two materials to one another, so that elements of the expandable member are effectively embedded within a mass of inner and outer covering materials. When the inner and outer materials are the same, then the expandable member elements become embedded in a mass of the same material.

Again, in these embodiments of the invention, the covering materials used may have a relatively conformable state during a time in which they are forced against the expandable member elements and against themselves, and then be attached and converted to a less conformable state. The covering materials can thereby locally contour to elements of the expandable member while in a conformable state, and upon attachment to each other will effectively and closely embed the expandable member elements. Again, in these aspects of the invention, the preferred covering materials will be hydratable, and will be relatively more conformable when hydrated than when dried. The covering material while hydrated state can thus be forced against an inner and/or outer surface of the expandable member, and attached and dried. Advantageously, a vacuum pressing operation can be utilized to both force the covering material against the expandable member and to dry the covering material. Also advantageously, the covering material(s) is/are desirably of a character so as to form an attachment to one another by virtue of being dried while compressed against each other. For example, the covering materials can each include a collagenous material, especially a collagenous extracellular matrix material. Dehydration of the collagenous materials in forced contact with one another effectively bonds the materials to one another, even in the absence of other agents for achieving a bond, although such agents can be used while also taking advantage at least in part on the dehydration-induced bonding. With sufficient compression and dehydration, the two collagenous covering materials can be caused to form a generally unitary collagenous structure embedding the expandable member elements. Vacuum pressing operations, and the closely embedded nature that they can characteristically impart to the covering material(s) and expandable member element(s), are highly advantageous and preferred in these aspects of the invention.

In this regard, suitable equipment for use for vacuum pressing in the present invention can be commercially obtained. One such vacuum pressing apparatus is commercially available from Zip-Vac East, Incorporated, Kennesaw, Ga. This vacuum pressing apparatus has a flexible chamber that has a vacuum drawn on it, which pulls the flexible boundaries of the chamber onto and around the article in the chamber. The vacuum also removes water from hydrated materials within the chamber.

It is advantageous to use a bioremodelable material for covering material(s) in the present invention, and particular advantage can be provided by coverings including a bioremodelable collagenous material. Such bioremodelable collagenous materials can be provided, for example, by collagenous materials isolated from a suitable tissue source from a warm-blooded vertebrate, and especially a mammal. Such isolated collagenous material can be processed so as to have bioremodelable properties and promote cellular invasion and ingrowth. Bioremodelable materials may be used in this context to promote cellular growth within the lumen of a vessel in which a medical device of the invention is implanted.

Suitable bioremodelable materials can be provided by collagenous extracellular matrix materials (ECMs) possessing biotropic properties. For example, suitable collagenous materials include ECMs such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa.

As prepared and used, the ECM and any other collagenous material used, may optionally retain growth factors or other bioactive components native to the source tissue. For example, submucosa or other ECMs may include one or more growth factors such as basic fibroblast growth factor (FGF-2), transforming growth factor beta (TGF-beta), epidermal growth factor (EGF), and/or platelet derived growth factor (PDGF). As well, submucosa or other ECM when used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the material used for the covering. These non-native bioactive components may be naturally-derived or recombinantly produced proteins that correspond to those natively occurring in an ECM tissue, but perhaps of a different species (e.g. human proteins applied to collagenous ECMs from other animals, such as pigs). The non-native bioactive components may also be drug substances. Illustrative drug substances that may be incorporated into and/or onto the covering materials include, for example, anti-clotting agents, e.g. heparin, antibiotics, and anti-proliferative agents, e.g. taxol derivatives such as paclitaxel.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

Biocompatible synthetic polymeric materials may also be used as covering materials in aspects of the present invention. For example, the polymeric material may be bioresorbable, or non-bioresorbable. Bioresorbable materials provide advantages in many circumstances and may include, for example, poly (lactic acid), poly (glycolic acid), copolymers thereof, or other suitable known materials.

Turning now to a discussion of the illustrative embodiments depicted in the Figures, shown in FIG. 1 is a perspective, partial cut-away view of one expandable graft device 11 of the invention. Expandable graft device 11 generally includes a bioremodelable covering 12, and a stent 13 (partially shown in the cut-away portion of covering 12), for example a Zilver® stent, embedded within the covering 12. Expandable graft device 11 thus includes an outer surface 14 and an inner lumenal surface 15 defined by the bioremodelable covering 12. In this manner, unless another material is used to provide a further coating or covering over the outer surface 14, upon implantation, the outer surface 14 will contact the tissue in the surrounding lumen and will be remodeled from that tissue. As well, unless another material is used to provide a further coating or covering over inner lumenal surface 15, inner lumenal surface of lumen 16 will contact any fluid flowing through the vessel in which device 11 is implanted, for example blood when the expandable graft device 11 is a vascular implant. In the illustrated embodiment, the covering 12 embedding the stent 13 is made from the same material on portions occurring inside and outside of the embedded stent, desirably a material including submucosa, such as small intestinal submucosa, or another ECM material.

Figure 2:
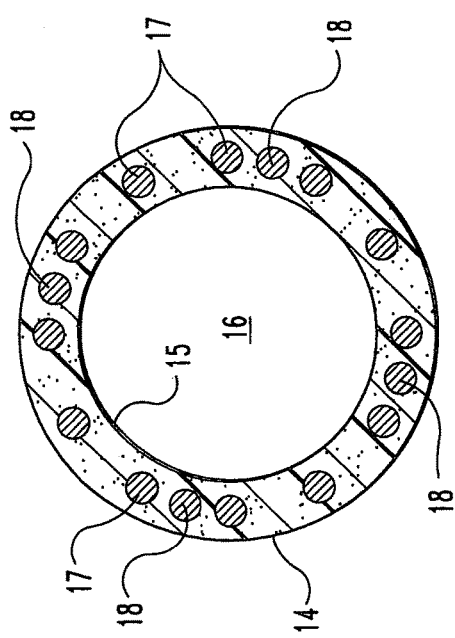
FIG. 2 provides a cross-sectional view taken along line 2-2 of FIG. 1 and viewed in the direction of the arrows.

With reference to FIG. 2, shown is a cross-sectional view taken along line 2-2 of FIG. 1 and viewed in the direction of the arrows. Shown is covering 12 embedding elements 17 of stent 13 forming generally serpentine cells, and elements 18 of stent 13 connecting adjacent cells. While covering 12 is shown in this illustration as a homogenous member, it will be understood that when elements 17 are embedded by being captured between inner and outer bonded layers, there may be some demarcation of the boundary between the bonded layers, either visible upon gross inspection and/or upon microscopic examination. As well, the covering 12 may include bonded layers of differing materials, for example with one layer being a collagenous (e.g. ECM) layer, and another being a different collagenous (e.g. ECM) layer or a bioresorbable or non-bioresorbable synthetic polymeric material. In one illustrative example, an inner bonded layer may be provided by renal capsule membrane or another non-submucosa ECM material, while an outer bonded layer may be provided by submucosa.

Figure 3:
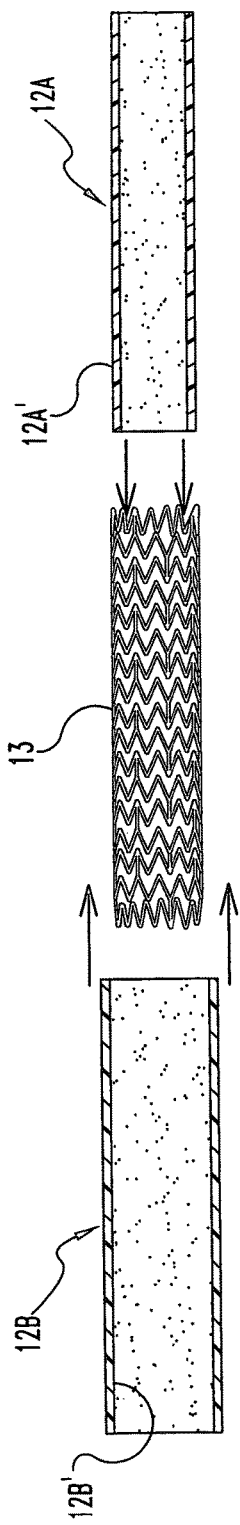
FIGS. 3-5 illustrate one mode of assembly and components in the manufacture of a stent graft device of the invention.
Figure 4:
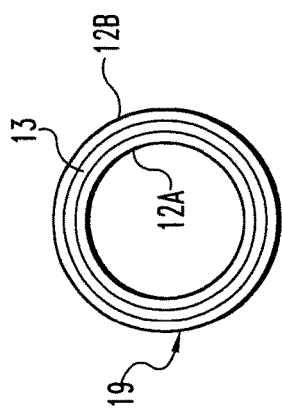

Referring now to FIGS. 3 and 4, illustrated are components that may be used in the manufacture of expandable graft device 11 depicted in FIGS. 1 and 2. A first tube of covering material 12A and a second tube of covering material 12B are provided. Tubes 12A and 12B may, for example, be prepared from sheet material, for example sheet-form ECM, or may be manufactured as a tubular material or isolated as a tubular material, e.g. in the case of an isolated tubular ECM material such as submucosa retaining its native tubular form. Tube 12A has an outer diameter such that it can be positioned within the lumen of stent 13. Tube 12B has an inner diameter such that it can be positioned over the outer surface of stent 13. The resulting assembly, as shown in FIG. 4, includes tube 12A within stent 13 within tube 12B. Bonding of areas of the outer surface 12A' of tube 12A that contact the inner surface 12B' of tube 12B to one another effectively entraps the stent 13 in a covering comprised of tubes 12A and 12B.

Figure 5:
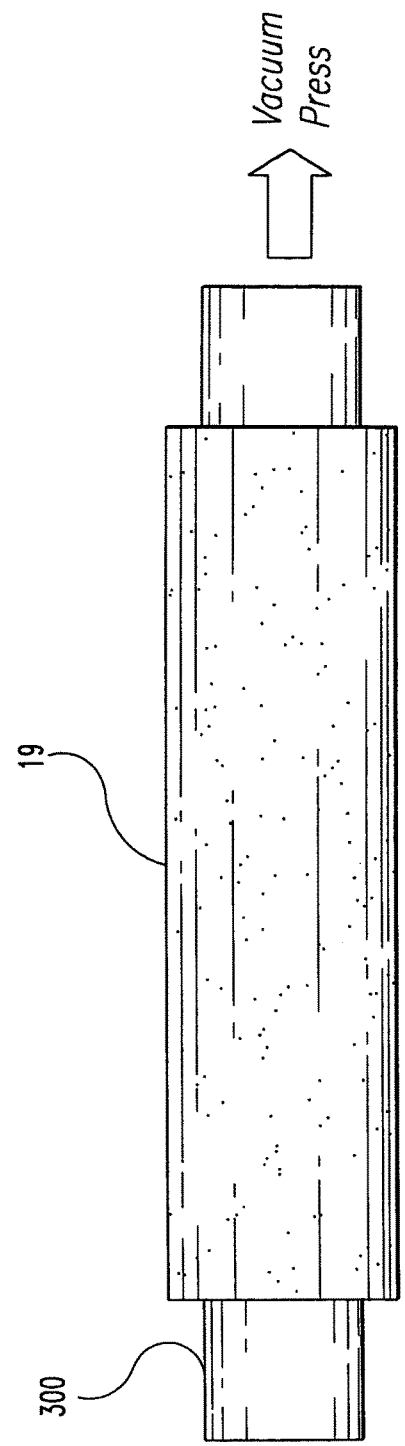

FIG. 5 shows a graft/mandrel assembly 19, including inner cover 12A, stent 13, and outer cover 12B, mounted over mandrel 300. This assembly 19 can be prepared in one manner of manufacturing a finished expandable graft device 11. While the illustrated assembly includes mandrel 300, e.g. a glass or stainless steel mandrel, the assembly 19 could also be mounted over another article conforming to the inner lumen of the assembly. The tubes 12A and 12B can be hydrated before and/or after placement on the mandrel 300. As well, a non-stick material, such as Teflon tape or a lubricant, can be applied to the outer surface of mandrel if needed to facilitate removal of the device 11 from the mandrel after processing. The graft/mandrel assembly is then placed in the chamber of a vacuum pressing apparatus, and the apparatus is operated, resulting inn the close, tight conformance of the chamber to the exterior surfaces of the mandrel/graft assembly 19. After the operation is completed and the material of tubes 12A and 12B is substantially dried, the vacuum can be discontinued and the mandrel/graft assembly removed from the chamber. The graft device 11 can then be removed from the mandrel. Generally, the vacuum pressing operation can be conducted under heated, room temperature, or cooled conditions.

In other embodiments of the invention, a graft assembly 19 including hydrated bioremodelable covering material can be processed in other ways to entrap the stent 13 between covers 12A and 12B. For example, other drying methods may be employed while providing effective contact between areas of covers 12A and 12B. In certain forms of the invention, the drying method will include lyophilization, e.g. using freeze-drying or evaporative cooling conditions, as a part or all of the drying technique. Illustratively, assembly 19 may be mounted over a cylindrical member such as a tube or mandrel, and force applied to the external surfaces of assembly 19 during lyophilization, so as to increase the bonded relationship of cover 12A and cover 12B. In such operations, either the cylindrical member, or the mechanism or material used to apply external force, or both, will be of a nature to permit the lyophilization process to occur, thus drying the covers 12A and 12B. For example, to apply external pressure to the assembly 19, it may be wrapped or encased tightly within an apertured, porous or otherwise water vapor-permeable material. In addition or alternatively, the cylindrical member, e.g. a tubular member, may be permeable to water vapor, e.g. due to apertures or pores in the member. These and other methods for providing close contact between surfaces of cover materials 12A and 12B during lyophilization will be available to those skilled in the art and are contemplated as being within the scope of the present invention.

It has been discovered that conditions of lyophilization can be used to provide collagenous covering materials of relatively higher pliability upon rehydration than those resulting from other, higher-temperature drying procedures such as room- or elevated-temperature vacuum-pressing. Accordingly, in certain forms of the invention, graft assembly 19 will be lyophilized at some point in the manufacturing procedure. For example, a hybrid drying procedure can be employed, in which assembly 19 is vacuum pressed for a period of time and under conditions to achieve partial drying and at least some bonding of the covering materials 12A and 12B to one another, and then the drying of the assembly 19 can be completed under conditions of lyophilization, which may also contribute to the bonding process. Thereafter, if desired, the assembly 19 can be rehydrated, configured to its collapsed condition, and dried again, advantageously again by lyophilization.

In other processes, assembly 19 is first vacuum pressed to substantial dryness, thereby bonding covers 12A and 12B. Assembly 19, or at least the covering 12 (FIG. 1) formed by bonded covers 12A and 12B, is thereafter rehydrated and lyophilized so as to increase the pliability or flexibility of covering 12 upon rehydration relative to that possessed by the covering 12 after the vacuum pressing operation. Again, if desired, the assembly 19 can thereafter be rehydrated, configured to its collapsed condition, and dried again, advantageously again by lyophilization.

Embodiments of the invention also encompass expandable graft devices including an expandable member and covering material located only on the inner or outer surface of the expandable member. Illustratively, with reference to FIG. 3, in certain embodiments, only one of tubes 12A and 12B is associated with the stent 13. Otherwise, the resulting graft/stent assembly can be processed in any manner as described above, or other similar manners. In these embodiments of the invention, the covering can be applied so as to achieve a close association between the covering and stent in which localized regions of covering 12A or 12B are locally contoured to surfaces of elements 17 and/or 18 of stent 13.

FIGS. 6A and 6B provide cross-sectional, cut-away views of wall portions of stent graft embodiments in which only external covering 12B is applied to stent 13. Shown in FIG. 6A is an embodiment in which the exterior surface 14 of the covering 12B retains a substantially smooth profile, whereas the opposed, inner surface contours closely around stent elements 17. This configuration may be achieved, for example, when the material of covering 12B is compressible, thus at least partially receiving elements 17 compressed into the wall thickness of covering 12B while maintaining a substantially smooth exterior profile. This configuration may also be effectively achieved where the diameters of elements 17 are sufficiently small in relation to the wall thickness of covering 12B, regardless of the level of compressibility possessed by covering 12B.

Shown in FIG. 6B is an embodiment in which the exterior surface 14 of the covering 12B has localized bumps, ridges or other proturbances overlying stent elements 17. This configuration may be achieved, for example, when the material of covering 12B is relatively incompressible, but sufficiently pliable to contour around stent elements 17. It may also be effectively achieved where the diameters of elements 17 are sufficiently large in relation to the wall thickness of covering 12 B, again regardless of the level of compressibility of covering 12B.

Figure 7A:
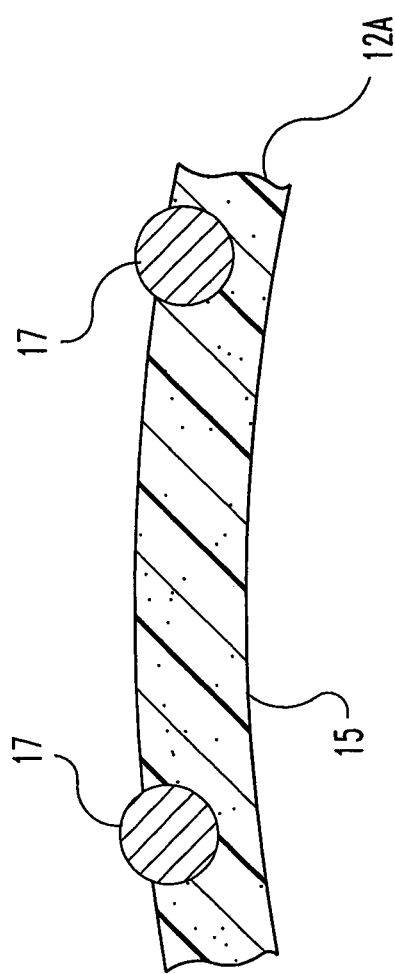
Figure 7B:
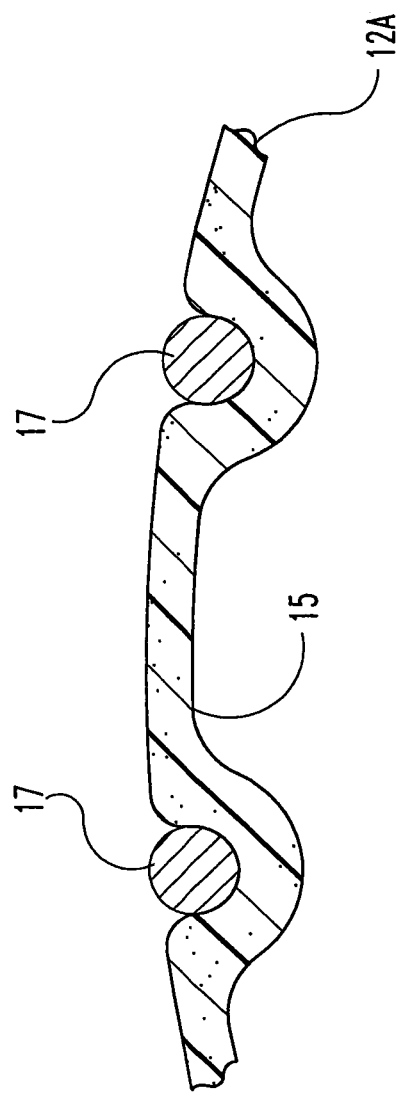

FIGS. 6A and 6B provide cross-sectional, cut-away views of wall portions of stent graft embodiments in which only internal covering 12A (FIG. 3) is applied to stent 13. The potential inner contours of covering 12A in FIGS. 7A and 7B generally correspond to the potential outer contours of covering 12B in FIGS. 6A and 6B, respectively. The potential outer contours of covering 12A in FIGS. 7A and 7B generally correspond to the potential inner contours of covering 12B in FIGS. 6A and 6B, respectively. Likewise, illustrative materials and situations under which the respective surface contours of covering 12A can be achieved correspond to those discussed above in connection with FIGS. 7A and 7B. Thus for the sake of brevity these details will not be specifically repeated here.

In a similar fashion, the inner and outer surface contours of inner and outer coverings 12A and 12B in entrapped or embedded versions such as stent graft device 11 may vary. Two such possibilities are shown in FIGS. 8A and 8B for purposes of illustration. It will be understood, as well, that other contours or combinations of contours may be provided. For example, a smooth inner contour of inner cover 12A (e.g. 12A of FIG. 8A) may exist in combination with a proturbance-containing outer contour of outer covering 12B (e.g. 12B of FIG. 8B); or, a smooth outer surface contour of cover 12B (e.g. 12B of FIG. 8A) may exist in combination with a proturbance-containing inner surface contour of cover 12A (e.g. 12A of FIG. 8B). Still further, various inner and outer surface contour combinations may be provided on different regions of the stent graft device.

Figure 11:
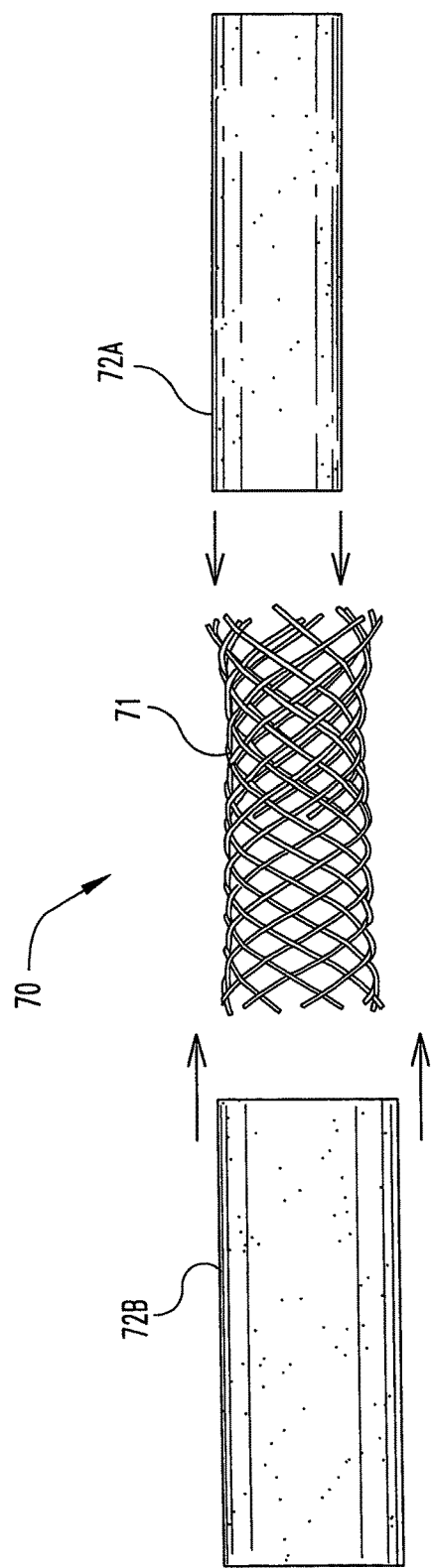

With reference to FIGS. 9, 10, and 11, shown are additional illustrative embodiments of the present invention, incorporating various types of stents into stent graft devices. Thus, stent graft device 50 may be prepared by processing stent 50 (illustrated as a known balloon-expandable clamshell-style stent) to apply covering 52A and/or covering 52B; stent graft device 60 may be prepared by processing stent 61 to apply covering 62A and/or covering 62B; and stent graft device 70 may be prepared by processing stent 71 to apply covering 72A and/or 72B. In all cases, illustrative modes of applying the covering(s) and resultant constructs can generally correspond to those discussed hereinabove with reference to expandable device 11.

Figure 12:
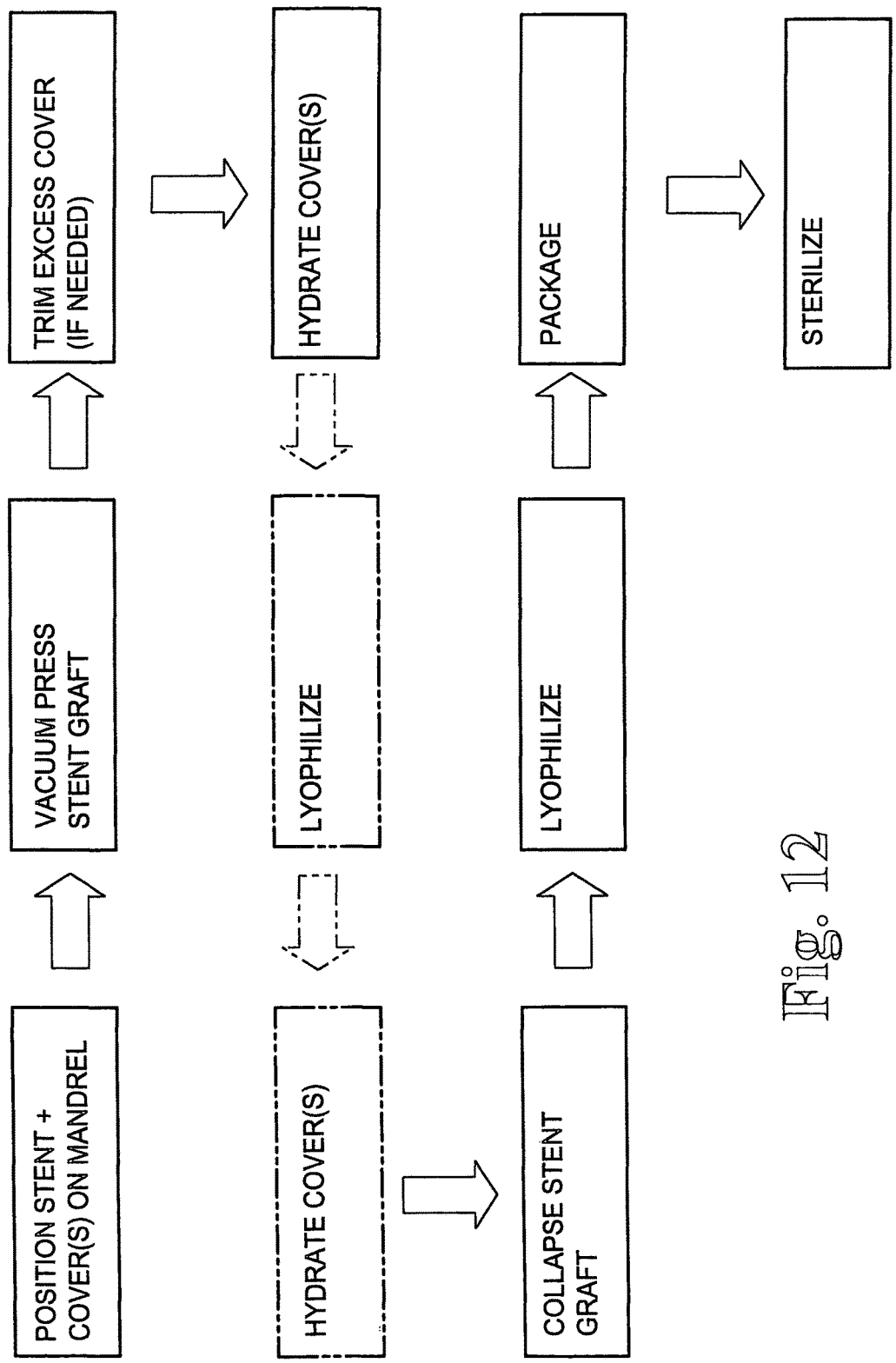
FIG. 12 provides a flow chart of an illustrative manufacturing method of the invention.

Referring now to FIG. 12, provided is an illustrative flowchart of one method of manufacturing stent graft devices in accordance with the invention. The stent and the partial and/or complete inner and/or outer covers are positioned on a mandrel or other conforming article. This assembly is vacuum pressed. Any excess covering material is trimmed, and the covering material(s) hydrated. In some forms of the invention, the hydrated assembly is then rendered to its collapsed condition without any intervening lyophilization. In other forms of the invention, as illustrated by the dotted-line elements of FIG. 12, the hydrated assembly is lyophilized and rehydrated prior to putting the assembly in its collapsed condition. As noted above, lyophilization can be conducted so as to provide a relatively more pliable covering material, including especially in the case of collagenous coverings such as ECM coverings. This increased pliability may ease the collapsing step, and/or may decrease the likelihood or extent of any damage that may occur to the covering material during the collapsing step and subsequent handling. After collapsing the stent graft assembly, it is then lyophilized in the collapsed state, after which it can be packaged in suitable medical packaging and sterilized. It will be understood that the above-described process or steps thereof are not limiting of broader expressions or aspects of the present invention, and that even within processes similar to those described, other operations may occur before, after or in between the steps described above, and/or that certain steps may be omitted or taken in different order. For example, any excess cover material can be trimmed at any suitable time within the manufacturing process, or even on-site during use of the stent graft device. Also, the stent graft device could be packaged and marketed after vacuum pressing, or after any hydration or lyophilization step, either in its expanded state to be loaded later, or in its contracted state (including hydrated or dried forms) unloaded or preloaded on or in a delivery device. As well, other pressure differential-based compression and drying operations may be used in place of or in addition to vacuum drying, including for instance forced air drying; and, hybrid drying techniques that utilize lyophilization conditions in combination with other drying conditions may be used to provide materials that are more pliable upon rehydration, consistent with the related discussions above. These and other modifications are possible within the scope of inventions as disclosed herein.

It is advantageous in some aspects of the invention to perform drying operations under relatively mild temperature exposure conditions that minimize deleterious effects upon components of the covering material(s), for example native collagen structures and potentially bioactive substances present, e.g. in the case of ECM-containing covering material(s). Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

With reference now to FIGS. 13 and 14, shown are two stent graft devices of the invention combined with delivery devices such as catheters. In this regard, FIG. 13 shows a medical apparatus 305 of the invention including expandable graft device 11 (FIG. 1), which is a self-expanding device, received within the lumen 307 of delivery catheter 306. In this illustration, device 11 is in its contracted state, and can be deployed by forcing the device 11 out of an opening of the catheter 11, for example with a push rod or other suitable mechanism. Upon deployment, device 11 conforms to the inner walls of the bodily lumen into which it is implanted.

FIG. 14 shows a medical apparatus 310 of the invention including balloon-expandable stent graft 50 (FIG. 9) received in its contracted configuration overtop expandable balloon 312 of balloon catheter 311. Deployment of device 50 can be conducted in the convention fashion, by expanding balloon 312 so as to deform the stent 51 so as to conform to the inner walls of the bodily lumen.

Figure 15:
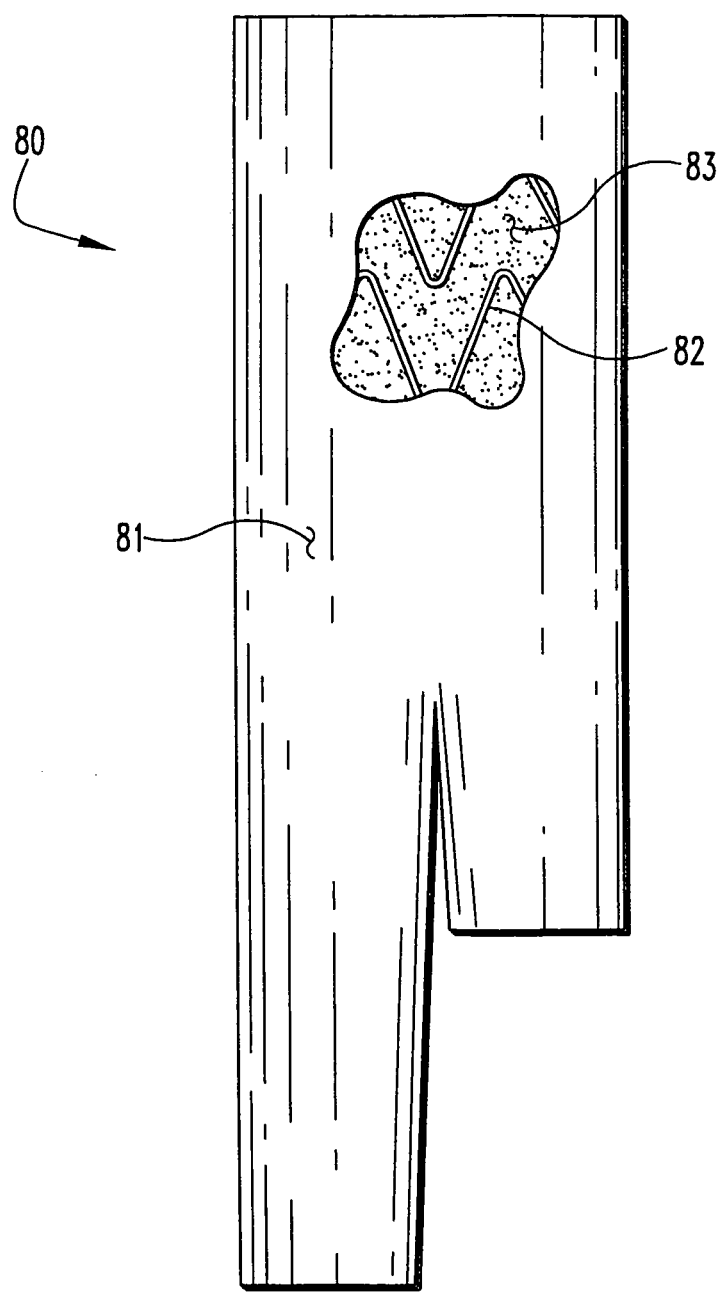
FIG. 15 illustrates another stent graft embodiment of the present invention.

FIG. 15 provides a partial cut-away perspective view of another stent graft device 80 of the invention. Device 80 includes a first, larger lumen, that directs its flow into two smaller lumens, as illustrated. Device 80, in this regard, may be generally similar to the graft body provided in the Zenith® endovascular graft available from Cook, Inc, Bloomington, Ind. Device 80, however, can include an outer covering material 81, and/or an inner covering material 83, applied to a plurality of stents 82 including generally serpentine elements, in a manner or to have a character as described in connection with the embodiments above. In stent graft device 80 and potentially in other stent graft designs disclosed herein a plurality of separate and discrete stent elements (e.g. 82) can be interconnected by the covering material and entrapping, bonding and other methods described herein to form a unitary graft device, representing additional aspects of the invention. Such interconnections can be achieved by any suitable methods, and may include the use of inner and outer covering material layers that are single more multilaminate constructs, e.g. multilaminate bioremodelable ECM or other constructs as described herein. In this regard, the lamination of the layers in the multilaminate constructs can occur prior to and/or during the application of the covering materials to the stented graft constructs of the invention. As well, any suitable arrangement of one or more pieces of covering material that results in a stable interconnection of the stents may be used. In this regard, a single tube or other piece of covering material could be wrapped inside and outside the multiple stent to interconnect them, separate tubes or other pieces (each tube or piece single or multilaminate) could be used inside and/or outside, etc. Furthermore, it would not be necessary for any single piece to extend completely between any two of the stents in the assembly (although this is certainly possible and advantageous in some respects), as covering material pieces contacting respective spaced stents could be arranged to overlap one another in regions spanning between the spaced stents and nonetheless provide for an effective interconnection of the stents in the final construct. As to the number of stents in the overall construct, this will depend upon the intended application of the final device and required properties; however, constructs having anywhere from two to thirty or more stents, which may be the same or may differ from one another and may be radially expandable or fixed, are contemplated as being a part of the present invention. These and other alternatives will be apparent to those skilled in the art from the descriptions herein.

Figure 16:
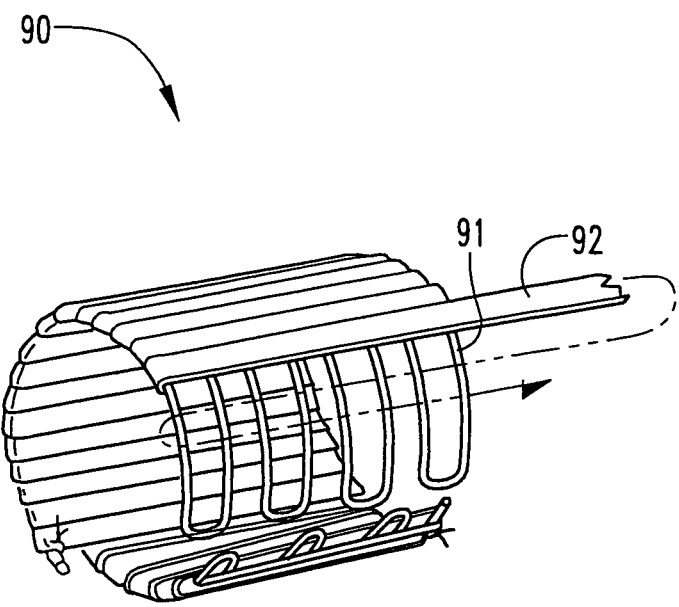
FIG. 16 illustrates another stent graft embodiment of the present invention.
Figure 17:
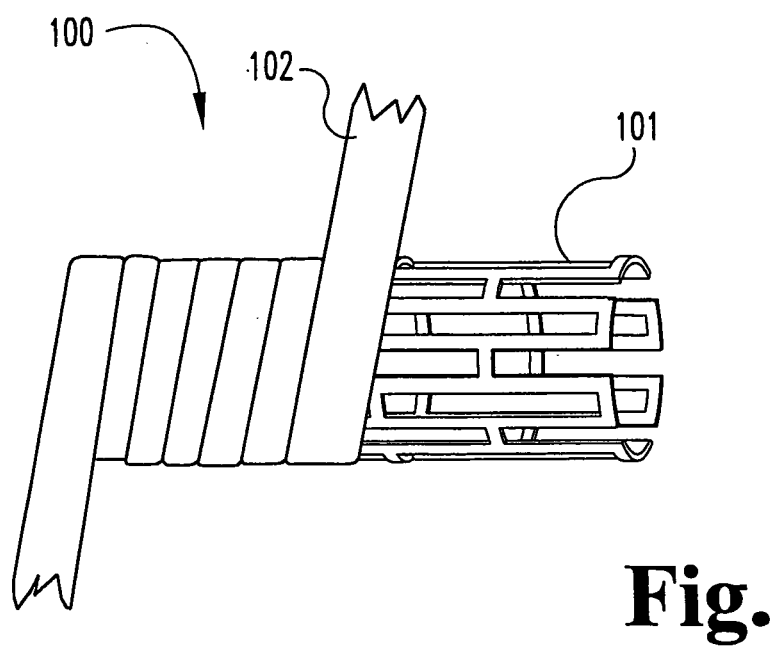
FIG. 17 illustrates another stent graft embodiment of the present invention.

Referring to FIGS. 16 and 17, additional illustrative constructs and practices within the invention are shown, in which sheets of covering material (especially bioremodelable material such as collagenous ECM material), in non-tube form, are applied over stent devices to provide internal and/or external covers. Thus, shown in FIG. 16 is a point in the manufacture of stent graft device 90, wherein a strip-form sheet of covering material is wound longitudinally through and around the outside of stent device 91, overlapping the longitudinal passes of the strip in each winding. In this fashion, covering material can be applied to the internal and external surfaces of all or a portion of the stent 91. After completing the winding application, the internal and external portions of the covering material can be bonded to each other as described herein, to form stent graft device 90 with elements of stent 91 entrapped or embedded within the covering material 92.

FIG. 17 shows an embodiment 100 in which an external layer of covering material 102 is provided on stent 101 by winding a strip-form sheet of covering material 102 over the outer surface of stent 101, while overlapping the windings. Again, the covering material 102 may be applied to cover all or a portion of the external surface of stent 101, and the stent processed as described hereinabove to associate the covering material 102 with the stent 101.

Figure 18:
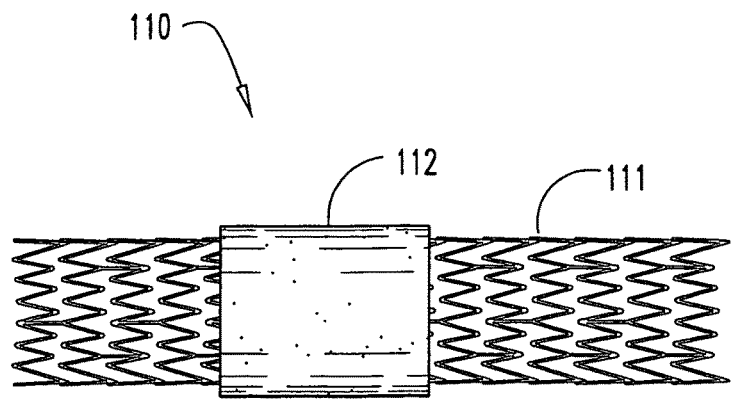
FIG. 18 illustrates another stent graft embodiment of the present invention.
Figure 19:
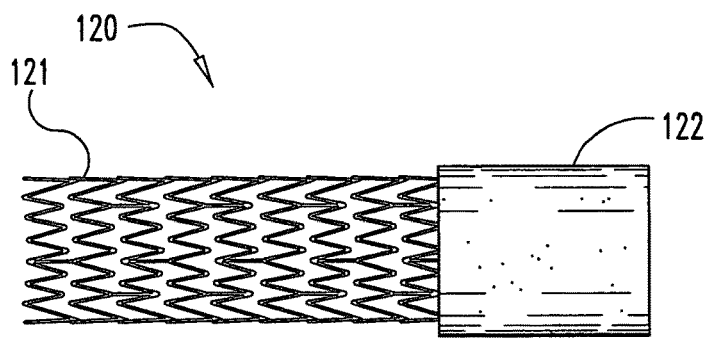
FIG. 19 illustrates another stent graft embodiment of the present invention.
Figure 20:
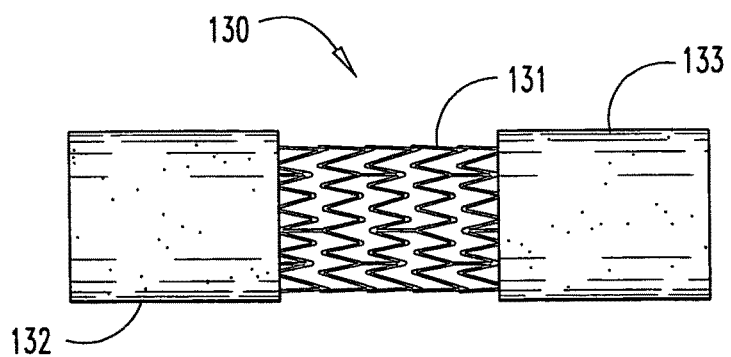
FIG. 20 illustrates another stent graft embodiment of the present invention.

FIGS. 18, 19 and 20 are provided to illustrate embodiments of the invention wherein covering material is applied to only a portion of the internal and/or external surface of the stent. Specifically, shown in FIG. 18 is stent graft device 110 including a stent 111 and a region of covering 112 located between two uncovered regions of the stent 111. FIG. 19 shows a stent graft device 120 in which a covered region 122 spans from one end of a stent 121 to a point along the length of the stent, with the remainder of the stent uncovered. FIG. 20 shows a stent graft device 130 in which an uncovered region 131 is flanked by two covered regions 132 and 133. Covered Regions 112, 122, 132 and 133 as illustrated in FIGS. 18, 19 and 20, may represent external coverings only, or both internal and external coverings. In addition, covered regions such as 122, 132 and 133 that extend to an end of the stent, may include both internal and external covers provided by a single tube of material everted around the end of the stent and processed as described herein; this everted tube technique may also be used to provide a complete cover to the inside and outside of the stent, or to provide a cover completely over the inside or outside of the stent, and partially over the other side, as would be the case in a covering on the entire inside or outside and everting to the opposite side on each end only for an amount sufficient to achieve an entrapped or embedded attachment of stent elements at the ends of the stent, thereby securing the covering. As well, it will be understood that similar regions could be covered only internally, and that the coverings in these areas may extend only partially around the circumference of the stents or completely around the circumferences of the stents.

In forms of the invention, the coverings provided on the stent graft devices will be relatively thick. For example, in the case of ECM coverings, multilaminate materials may be used for the inner and/or the outer covering(s). Thus, multilaminate constructs including two, three, four, five or six or more bonded layers of ECM material, such as submucosa, may be used as inner and/or outer covering materials. Such materials may benefically provide relatively higher quantities of bioremodelable material, as well as advantageous physical and mechanical properties, including as one example higher resistance to the formation of pin-holes or other cracks or punctures during processing and use, where such resistance is desired. Such thicker covering materials may also provide additional mass to more effectively contour to and/or entrap or embed elements of the associated stents.

In one embodiment of the invention, the wall thickness of a covering material applied as an internal or external covering will be at least about 150 microns, with this measure representing the hydrated form of hydratable materials such as collagenous ECM materials, e.g. submucosa. In other embodiments, this wall thickness will be at least about 200 microns, for example in the range of about 200 to about 600 microns. In cases where elements of the stent are entrapped or embedded within covering materials on both inner and outer surfaces of the stent, the total thickness of the inner and outer covering materials combined can likewise be at least about 150 microns, and in some cases at least about 200 microns, for example from about 200 to about 600 microns, with these measures again representing the hydrated form of hydrdatable materials such as collagenous ECM materials, e.g. submucosa.

In accordance with aspects of the invention, an adhesive, glue, adherent polymer or other bonding agent may be used in achieving a bond between covering materials located inside and outside of the stent, and/or between covering material and elements of the stent. Suitable bonding agents may include, for example, collagen gels, gelatin, fibrin glue, or other agents including reactive monomers or polymers, for example cyanoacrylate adhesives. As well, bonding between collagenous covering materials can be achieved or facilitated using chemical crosslinking agents, such as glutaraldehyde, carbodiimide compounds, polyepoxide compounds, or other similar agents, as well as radiative energy-induced crosslinking for example imparted by UV radiation. The combination of one or more of these with dehydration-induced bonding may also be used.

It will be understood that covering materials applied using the techniques described above may also be attached at some locations to the stent using other mechanisms, e.g. sutures. It will also be understood that other covering materials may be applied to the stent in addition to inner and outer covering materials applied as described above. For example, one of an inner or outer covering material may be applied as described above, and the other applied using other mechanisms, for example by mechanical attachment such as suturing. As well, other covering materials may be sutured or otherwise attached overtop of covering materials applied as described herein, to partially or completely encompass the applied covering materials. These and other modifications will be available to the skilled artisan.

Expandable graft devices can be configured for and used in a variety of bodily lumens, including as examples those in the vascular system such as arteries and veins, urethra, ureter, bile duct, trachea, esophagus, bowel, and others.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The following US patents and other publications, and all other publications cited herein, are hereby incorporated herein by reference in their entirety as if each had been individually incorporated by reference and fully set forth: U.S. Pat. No. 4,902,508, Tissue Graft Composition; U.S. Pat. No. 4,956,178, Tissue Graft Composition; U.S. Pat. No. 5,275,826, Fluidized Intestinal Submucosa and its Use as an Injectable Tissue Graft; U.S. Pat. No. 5,281,422, Graft For Promoting Autogenous Tissue Growth; U.S. Pat. No. 5,352,463, Tissue Graft for Surgical Reconstruction of a Collagenous Meniscus And Method Therefor; U.S. Pat. No. 5,372,821, Graft for Promoting Autogenous Tissue Growth; U.S. Pat. No. 5,445,833, Tendon or Ligament Graft for Promoting Autogenous Tissue Growth; U.S. Pat. No. 5,516,533, Fluidized Intestinal Submucosa and its Use as an Injectable Tissue Graft; U.S. Pat. No. 5,573,784, Graft for Promoting Autogenous Tissue Growth; U.S. Pat. No. 5,641,518, Method of Repairing Bone Tissue; U.S. Pat. No. 5,645,860, Tissue Graft and Method for Urinary Urothelium Reconstruction Replacement; U.S. Pat. No. 5,695,998, Submucosa as a Growth Substrate for Islet Cells; U.S. Pat. No. 5,711,969, Large Area Submucosal Tissue Graft Constructs; U.S. Pat. No. 5,753,267, Method for Enhancing Functional Properties of Submucosal Tissue Graft Constructs; U.S. Pat. No. 5,755,791, Perforated Submucosal Tissue Graft Constructs; U.S. Pat. No. 5,762,966, Tissue Graft and Method for Urinary Urothelium Reconstruction Replacement, U.S. Pat. No. 5,866,414, Submucosa Gel as a Growth Substrate for Cells; U.S. Pat. No. 5,885,619, Large Area Submucosal Tissue Graft Constructs and Method for Making the Same; U.S. Pat. No. 5,711,969, Multilayered Submucosal Graft Constructs and Method for Making Same; U.S. Pat. No. 5,755,791, Method of Repairing Perforated submucosal Tissue Graft Constructs; U.S. Pat. No. 5,997,575, Perforated Submucosal Tissue Graft Constructs; U.S. Pat. No. 6,087,157, Device and Method of Analyzing Tumor Cell Invasion of an Extracellular Matrix; U.S. Pat. No. 6,096,347, Myocardial Graft Constructs; U.S. Pat. No. 6,126,686, Artificial Vascular Valves; U.S. Pat. No. 6,187,039, Tubular Submucosal Graft Constructs; U.S. Pat. No. 6,241,981, Composition and Method for Repairing Neurological Tissue; U.S. Pat. No. 6,264,992, Submucosa as a Growth Substrate for Cells; U.S. Pat. No. 6,331,319, Galactosidase Modified Submucosal Tissue; U.S. Pat. No. 6,375,989, Submucosa Extracts; U.S. Pat. No. 6,206,931, Graft Prosthesis Materials; U.S. Pat. No. 6,358,284, Tubular Grafts from Purified Submucosa; U.S. Pat. No. 5,554,389, Urinary Bladder Submucosa Derived Tissue Graft; U.S. Pat. No. 6,099,567, Stomach Submucosa Derived Tissue Graft; U.S. Pat. No. 6,666,892, Multi-formed Collagenous Biomaterial Medical Device; U.S. Pat. No. 6,358,284, Tubular Grafts from Purified Submucosa; U.S. Pat. No. 6,206,931, Graft Prosthesis Materials; US Publication No. US 20030051735A1, Vessel Closure Member, Delivery Apparatus, and Method of Inserting the Member 2003 March 2020; the following World Intellectual Property Organization publications identified by the publication numbers, titles, and publication dates: WO 03092546A2, Sling for Supporting Tissue, Nov. 13, 2003; WO 03092471A2, Cell-Seeded Extracellular Matrix Grafts, Nov. 13, 2003; WO 03088844A1, Apparatus and Method for Producing a Reinforced Surgical Staple Line, Oct. 30, 2003; WO 03035125A3, Medical Graft Device with Meshed Structure, May 1, 2003; WO 03035125A2, Medical Graft Device with Meshed Structure, May 1, 2003; WO 03009764A1, Vessel Closure Member and Delivery Apparatus, Feb. 6, 2003; WO 03002168A1, Porous Sponge Matrix Medical Devices and Methods, Jan. 9, 2003; WO 03002165A1, Graft Prosthesis Devices Containing Renal Capsule Collagen, Jan. 9, 2003; WO 0156500A, Implantable Vascular Device, Aug. 9, 2001; WO 0154625A1, Stent Valves and Uses of Same, Aug. 2, 2001; WO 0110355A1, Tubular Graft Construct, Feb. 15, 2001; WO 0032253A1, Radiopaque Implantable Collagenous Biomaterial Device, Jun. 8, 2000; WO 0032250A1, A Multi-formed Collagenous Biomaterial Medical Device, Jun. 8, 2000; and WO 0032112A1, Embolization Device, Jun. 8, 2000.

What is claimed is:

1. A unitary, implantable stent graft device, comprising:
a unitary graft body having an expanded configuration for deployment, and a collapsed configuration for delivery, said unitary graft body in said expanded configuration including:
  (i) a first graft segment defining a first inner lumen having a first diameter, the first graft segment having a first end;
  (ii) a second graft segment and a third graft segment branching from the first end of the first graft segment, the second graft segment defining a second inner lumen having a second diameter and the third graft segment defining a third inner lumen having a third diameter, wherein the second inner lumen and third inner lumen are in fluid communication with the first inner lumen, and wherein the second diameter and the third diameter are smaller than the first diameter;
  (iii) a plurality of discrete, spaced radially expandable stents positioned in said first graft segment;
  (iv) an exterior lyophilized collagenous covering situated to the exterior of said stents, said exterior lyophilized collagenous covering being comprised of an extracellular matrix material retaining growth factors from a source tissue for the extracellular matrix material, said exterior lyophilized collagenous covering promoting cellular invasion and ingrowth when implanted, and said exterior lyophilized collagenous covering forming a first continuous circumferential tube of material surrounding the exterior of said stents, the first continuous circumferential tube of material defining a continuous circumferential outer surface of said first graft segment;
  (v) an interior lyophilized collagenous covering situated to the interior of said stents, said interior lyophilized collagenous covering being comprised of an extracellular matrix material retaining growth factors from a source tissue for the extracellular matrix material, said interior lyophilized collagenous covering being a compressible material that includes an inwardly facing surface and an outwardly facing surface, said interior lyophilized collagenous covering promoting cellular invasion and ingrowth when implanted, and said interior lyophilized collagenous covering forming a second continuous circumferential tube of material surrounding the interior of said stents, the second continuous circumferential tube of material defining a continuous circumferential inner surface of said first graft segment and having been dehydrothermally bonded to said exterior lyophilized collagenous covering in the absence of other bonding agents;
  (vi) said exterior lyophilized collagenous covering having inwardly facing surface regions that face toward and are bonded to the outwardly facing surface of said interior lyophilized collagenous covering which includes bonding in areas between adjacent stents of said plurality of stents so as to entrap the stents between said first continuous circumferential tube of material and said second continuous circumferential tube of material;
  (vii) wherein strut elements of said stents are in contact with the outwardly facing surface of the interior lyophilized collagenous covering; and
  (viii) wherein the strut elements of the stents are compressed into the interior lyophilized collagenous covering such that said outwardly facing surface of said interior lyophilized collagenous covering has regions locally contoured to the strut elements, such that a wall thickness of said interior lyophilized collagenous covering is less where said interior lyophilized collagenous covering passes over the strut elements as compared to adjacent regions of the interior lyophilized collagenous covering occurring between the strut elements, and further such that the inwardly facing surface of the interior lyophilized collagenous covering has a smooth contour lacking protuberances in regions where the interior lyophilized collagenous covering passes over and between strut elements of the stents.

2. The stent graft device of claim 1, wherein said exterior lyophilized collagenous covering and said interior lyophilized collagenous covering have been provided by vacuum pressing an exterior collagenous covering material and an interior collagenous covering material followed by hydration and lyophilization of the exterior collagenous covering material and the interior collagenous covering material.

3. The stent graft device of claim 2, wherein said growth factors include basic fibroblast growth factor.

4. The stent graft device of claim 3, wherein said extracellular matrix material comprises submucosa.

5. The stent graft device of claim 1, wherein at least one of said exterior lyophilized collagenous covering and interior lyophilized collagenous covering includes a multilaminate construct.

6. The stent graft device of claim 5, wherein each of said exterior lyophilized collagenous covering and interior lyophilized collagenous covering includes a multilaminate construct formed of multiple covering material pieces.

7. The stent graft device of claim 6, wherein pieces of said multiple covering material pieces are arranged to contact respective spaced stents of said plurality of stents and to have ends that overlap one another in a region spanning between the respective spaced stents.

8. The stent graft device of claim 1, wherein said exterior lyophilized collagenous covering and interior lyophilized collagenous covering form a unitary collagenous structure embedding the stents and extending along the first graft segment, second graft segment and third graft segment.

9. The stent graft device of claim 1, wherein an outwardly-facing surface of the exterior lyophilized collagenous covering has protuberances in regions where the exterior lyophilized collagenous covering passes over strut elements of the stents.

10. The stent graft device of claim 1, which is a vascular stent graft device.

11. The stent graft device of claim 1, wherein the exterior lyophilized collagenous covering and interior lyophilized collagenous covering are bonded to one another over substantially all contacting areas of the two coverings such that the relation between the expandable stents and the bonded exterior lyophilized collagenous covering is fixed.

12. The stent graft device of claim 1, wherein an outwardly-facing exterior surface of the exterior lyophilized collagenous covering has a smooth contour lacking protuberances in regions where the exterior lyophilized collagenous covering passes over and spans between strut elements of the stents.

13. A stented graft construct, comprising:
a unitary graft body having an expanded configuration for deployment, and a collapsed configuration for delivery, said unitary graft body in said expanded configuration including:
 (i) a plurality of discrete, spaced stents spaced to provide openings between the stents; and
 (ii) said discrete, spaced stents interconnected to one another by inner and outer layers of a bioremodelable covering material that promote cellular invasion and ingrowth when implanted, wherein the inner and outer layers of bioremodelable covering material are each comprised of an extracellular matrix material retaining growth factors from a source tissue for the extracellular matrix material, wherein the inner and outer layers of bioremodelable covering material each form a continuous circumferential tube of material, wherein the inner and outer layers of bioremodelable covering material are sufficiently dehydrothermally bonded to one another in the absence of other bonding agents including through said openings to entrap the stents and form a stable, unitary stented graft construct for subsequent implantation in a patient, and wherein said inner layer of bioremodelable covering material is a compressible material that includes an inwardly facing surface and an outwardly facing surface, said outwardly facing surface being in contact with strut elements of said stents that are compressed into the inner layer of bioremodelable covering material such that said outwardly facing surface is contoured to the strut elements, such that a thickness of said inner layer of bioremodelable covering material is less where said inner layer of bioremodelable covering material passes over the strut elements as compared to adjacent regions of the inner layer of bioremodelable covering material that span between the strut elements, and further such that said inwardly facing surface has a smooth contour lacking protuberances in regions where said inner layer of bioremodelable covering material passes over and spans between the strut elements of said stents.

14. The stented graft construct of claim 13, wherein said inner and outer layers each include a multilaminate construct, wherein the outer layer is provided by submucosal extracellular matrix material, and wherein the inner layer is provided by non-submucosal extracellular matrix material.

15. The stented graft construct of claim 14, wherein said multilaminate construct includes a plurality of bonded extracellular matrix layers.

16. The stented graft construct of claim 13, wherein said stents are radially expandable stents.

17. The stented graft construct of claim 13, wherein the inner and outer layers of bioremodelable covering material are lyophilized and have been provided by bonding an inner layer of bioremodelable covering material and an outer layer of bioremodelable covering material to one another under vacuum pressing conditions followed by hydration and lyophilization of the inner layer of bioremodelable covering material and the outer layer of bioremodelable covering material.

18. The stented graft construct of claim 17, wherein said growth factors include basic fibroblast growth factor.

19. The stented graft construct of claim 18, wherein the bioremodelable covering material comprises submucosa.

20. The stented graft construct of claim 13, wherein the inner layer of bioremodelable covering and outer layer of bioremodelable covering material are bonded to one another over substantially all contacting areas of the two coverings such that the relation between the stents and the bonded inner layer of bioremodelable covering material and outer layer of bioremodelable covering material is fixed.

21. The stented graft construct of claim 13, wherein an outwardly-facing exterior surface of the outer layer of bioremodelable covering material has a smooth contour lacking protuberances in regions where the outer layer of bioremodelable covering material passes over and spans between strut elements of the stents.

22. The stented graft construct of claim 13, comprising a graft body including a first graft segment defining a first inner lumen, the first graft segment having a first end, with said plurality of discrete, spaced stents positioned in said first graft segment; and
the graft body also including a second graft segment and a third graft segment each branching from the first end of the first graft segment, the second graft segment defining a second inner lumen and the third graft segment defining a third inner lumen, wherein the second inner lumen and third inner lumen are in fluid communication with the first inner lumen.

23. A stented graft construct, comprising:
a unitary graft body having an expanded configuration for deployment, and a collapsed configuration for delivery, said unitary graft body in said expanded configuration including:
 (i) a plurality of discrete, spaced, serpentine stent elements in succession with openings between successive stent elements;
 (ii) said discrete, spaced stent elements interconnected to one another by being entrapped between inner and outer layers of a bioremodelable covering material that promotes cellular invasion and ingrowth when implanted, wherein the inner and outer layers of bioremodelable covering material are each comprised of an extracellular matrix material retaining growth factors from a source tissue for the extracellular matrix material, said inner and outer layers each forming a continuous circumferential tube of material, said inner and outer layers being dehydrothermally bonded to one another in the absence of other bonding agents including through said openings so as to provide a generally fixed association of said stent elements with the bioremodelable covering material, wherein the inner and outer layers are sufficiently bonded to one another to form a stable, unitary stented graft construct for subsequent implantation in a patient; and (iii) wherein said inner layer of bioremodelable covering material is a compressible material that includes an inwardly facing surface and an outwardly facing surface, said outwardly facing surface being in contact with strut elements of said stent elements that are compressed into the inner layer of bioremodelable covering material such that said outwardly facing surface is contoured to said strut elements, such that said inner layer of bioremodelable covering material has a wall thickness that is less where said inner layer of bioremodelable covering material passes over the strut elements as compared to adjacent regions of the inner layer of bioremodelable covering material that span between the strut elements, and further such that said inwardly facing surface has a smooth contour lacking protuberances in regions where said inner layer of bioremodelable covering material passes over and spans between the strut elements of said stent elements.

24. The stented graft construct of claim 23, wherein said inner and outer layers each includes a multilaminate construct.

25. The stented graft construct of claim 23, wherein said inner and outer layers are dehydrothermally bonded to one another by lyophilizing said inner and outer layers in contact with one another.

26. The stented graft construct of claim 23, wherein the inner and outer layers of bioremodelable covering material are lyophilized and have been provided by bonding an inner layer of bioremodelable covering material and an outer layer of bioremodelable covering material to one another under vacuum pressing conditions followed by hydration and lyophilization of the inner layer of bioremodelable covering material and the outer layer of bioremodelable covering material.

27. The stented graft construct of claim 23, wherein the outer layer of bioremodelable covering material and inner layer of bioremodelable covering material are bonded to one another over substantially all contacting areas of the two coverings such that the relation between the stent elements and the bonded outer layer of bioremodelable covering material and inner layer of bioremodelable covering material is fixed.

28. The stented graft construct of claim 23, wherein an outwardly-facing exterior surface of the outer layer of bioremodelable covering material has protuberances in regions where the outer layer of bioremodelable covering material passes over strut elements of the stents elements.

* * * * *